United States Patent [19]

Merskelly

[11] Patent Number: 5,352,211

[45] Date of Patent: Oct. 4, 1994

[54] EXTERNAL STABILITY DEVICE

[75] Inventor: William L. Merskelly, Xenia, Ohio

[73] Assignee: Louisville Laboratories, Louisville, Ky.

[21] Appl. No.: 86,010

[22] Filed: Jul. 11, 1993

[51] Int. Cl.⁵ .............................................. A61M 25/02
[52] U.S. Cl. ............................... 604/180; 128/DIG. 26
[58] Field of Search ............................. 604/174, 180; 128/DIG. 26

[56] References Cited

U.S. PATENT DOCUMENTS

| | | | |
|---|---|---|---|
| 3,138,158 | 6/1964 | Gordon et al. | 128/214 |
| 4,360,025 | 11/1982 | Edwards | 604/180 |
| 4,392,854 | 7/1983 | Ibach | 604/174 |
| 4,579,120 | 4/1986 | MacGregor | 604/180 |
| 4,699,616 | 10/1987 | Nowak et al. | 604/180 |
| 4,767,411 | 9/1988 | Edmunds | 604/180 |
| 4,874,380 | 10/1989 | Haskeith | 604/180 |
| 5,026,352 | 6/1991 | Anderson | 604/174 |
| 5,069,206 | 12/1991 | Crosbie | 604/174 |
| 5,073,169 | 12/1991 | Raiken | 604/180 |
| 5,137,520 | 8/1992 | Maxson et al. | 604/180 |

Primary Examiner—Paul J. Hirsch

[57] ABSTRACT

The present invention includes a flexible stability device for holding a medical device entering a body. The device includes a plurality of spaced apart flexible legs which extend from one side of a flexible planar member. The legs are clampable about the medical device.

20 Claims, 4 Drawing Sheets

EXTERNAL STABILITY DEVICE

BACKGROUND OF THE INVENTION (1) Field of the Invention

This invention relates to medical devices, and more particularly to body attachable clamps for securing medical devices to the body for delivering matter through a body wall.

(2) Prior Art

Transcutaneous placement of catheters or medical devices for the supply of medicaments and treatment of patients is a well developed field. Where the field still needs improvement is in the area of devices for anchoring those catheters or attached medical devices to the patient so that they will not come lose, the site will remain sterile, and that a certain amount of flexibility is permitted with respect to the patient. The prior art includes: U.S. Pat. No. 5,137,520 to Maxso et al., showing a rather inflexible device adaptable to only a particular size shaft; U.S. Patent to Ralken which unfortunately does not permit the opening in the patient to be sealed at the surface of the skin; U.S. Pat. No. 4,767,411 to Edmonds discloses a rather rigidly attached sleeve, which will not permit much flexibility; and. U.S. Pat. No. 4,392,854 to Ibach, which does permit flexibility, but does not seal the puncture site.

It is an object of the present invention to provide an external stability device which will allow for flexing of the catheter or attached medical device when necessary as the patient moves, will seal the puncture site if desired, and not allow contamination, and permits the use of different size shafts through the device, while the base of the stability device is still attached to the patient. It is a further object of the present invention to permit a stability device to be attachable to and removable from around an already inserted medical device.

BRIEF SUMMARY OF THE INVENTION

The present invention comprises a base and an attachable, articulable clamp matable with that base for securing medical devices such as tubes or the like where they pierce a body wall. The base unit is attachable to the skin of a patient into whom the medical device is to enter.

The base unit in the preferred embodiment comprises a flexible, thin annular disc having a central opening therein, The disc has an intermediate circumferential locus from which two pairs of diametrically arranged legs extend. A tab extends off of the distal end of each of the legs. The tabs, in the legs relaxed configuration, are parallel with the plane of the disc defining the lower portion of the base. It is to be noted that the flat planar base could be of triangular shape, of oval shape, multisided or otherwise, to accommodate desired locational or storage requirements.

Each leg is flexible, and is adaptable to flex radially inwardly so that the tabs may be shaped to form quarter segments of a circle. It is to be noted that the present invention could have any reasonable number of legs with appropriately arranged tabs thereattached.

A clamp portion of this invention comprises a unitary, injection molded 270 degree arc brace having articulable portions which connectively pull together the ends of the brace so as to form a full circle, having snap-lock engagement means to lock the braces together in that circular configuration. The clamp assembly is flexible enough to accomodate different shaped medical devices. The brace has an inner peripheral edge with a plurality of spaced apart retaining pins or buttons.

Each spaced apart button on the inside edge of the clamp is arranged to mate with a hole in each of the tabs of the flexed legs when these legs are bent together so that those tabs form a smaller circle when completely surrounded by the clamp.

The brace mates radially outwardly of the tabs, the tabs being disposable about a medical device which enters a body wall through the central opening in the middle of the disc. The brace, when it is locked about the tabs, holds any medical device therewithin, snugly.

The annular disc has a lower surface which may have a tissue engageable adhesive thereon. The disc is placed on a body surface, with its central opening arranged over the location where the medical device needs to pierce the body and extend outwardly therefrom. The base member as noted, may be of triangular, square or elongated peripheral shape, as long as the legs extend therefrom, and have tabs which are sandwiched between a medical device and the outer clamp holding them all together.

Thus, such a base and clamp assembly can support a medical device which has entered a body wall.

The invention comprises a stability device for holding a medical device member onto a patient, while permitting resilient flexibility and cleanliness of a surgical site, comprising a planar, flexible base having an central inner opening and an outer peripheral edge, a plurality of spaced apart flexible legs each extending from a location on one side said planar, flexible base, and a diametrically contractable clamp arrangable about the distal ends of the legs so as to enable a medical device to be securely engaged therewithin, the legs having a distal end with a tab extending therefrom, which tabs are disposed between the collapsable clamp and a medical device being secured therewithin, the resilient base having an adhesive disposed on one side thereof, to permit the stability device to be attached to a body. The stability device may be comprised of a thin circularly shaped disc. The clamp has an inner periphery with a plurality of buttons therein, buttons are arranged to engage the tabs in a secure manner. The clamp has a semicircular pivotable segment which has a locking member on its distal end, to engage a corresponding locking member also arranged on the clamp. The clamp is made of an injection molded plastic, in the open configuration of generally a figure "6" shape. The clamp is comprised of a first annular portion having a pair of ends which meet in abutting relationship when the semicircular segment is juxtaposed in locking relationship into the first annular portion.

The stability device comprises a flexible base arranged in a spaced relationship to a medical device entering a body surface, a plurality of spaced apart flexible legs extending from the flexible base, and a clamp means tightenable about the distal ends of the flexible legs so as to securely hold the legs onto any medical device disposed therewithin. The legs have a tab member disposed perpendicular thereto, on the distal end thereof. The clamp has a spaced array of buttons on its inner periphery, to engage the tabs on the legs. Each of the tabs has a hole therethrough for receipt of a button therein. The clamp has a locking means to hold it fixedly closed about the legs and a tubular member enclosed therewithin. The flexible base comprises a flexible planar portion, from which said flexible legs extend. The planar portion may be of generally circular disc shape, of generally triangular shape, or of multi-sided shape. The flexible base has a slit extending from its central opening outwardly therefrom to permit the base to be installed onto a medical device after that medical device is disposed in a patient. The invention also includes a method of applying a stability device to a patient prior to the patient having a medical device placed through a body wall. The steps for attaching the external stability device comprises: providing a spread open clamp around a flexible base member comprising a base of a stability device; providing the flexible, planar member with a plurality of flexible upstanding legs thereon and a central opening therethrough, the planar member having a slit extending from its central opening outwardly to its outer periphery; arranging the base member adjacent the medical device or tubing extending from the patient; spreading apart the flexible planar member on a slit to split thereacross, so as to engage the medical device in the central opening of the planar member; bending the flexible legs so that their distal ends engage the medical device; and pivot a closing clamp about distal ends of the legs so as to engage the device therewithin, and locking the clamp about the distal ends of the legs to engage the medical device therewithin.

BRIEF DESCRIPTION OF THE DRAWINGS

The objects and advantages of the present invention will become more apparent, when viewed in conjunction with the following drawings, in which.

DESCRIPTION OF THE PREFERRED EMBODIMENTS

Figure 1:
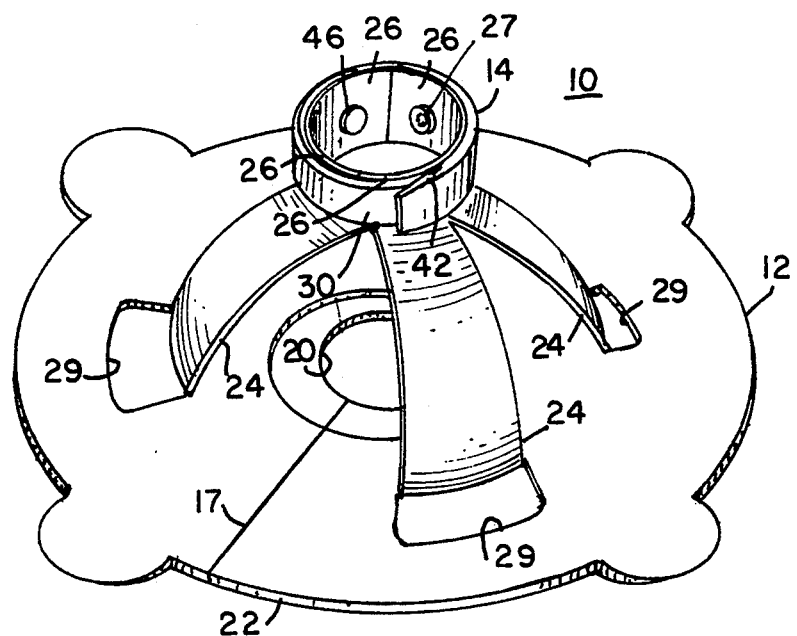
FIG. 1 is a perspective view of a stability device constructed according to the principles of the present invention.
Figure 2:
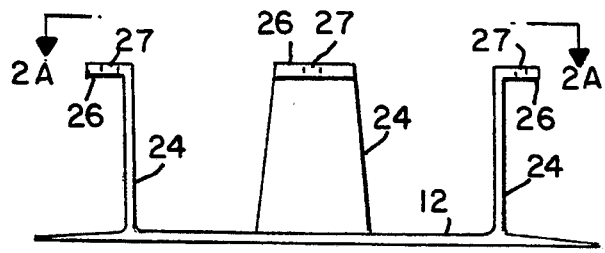
FIG. 2 is a side elevational view of a base unit in an unflexed orientation.
Figure 2A:
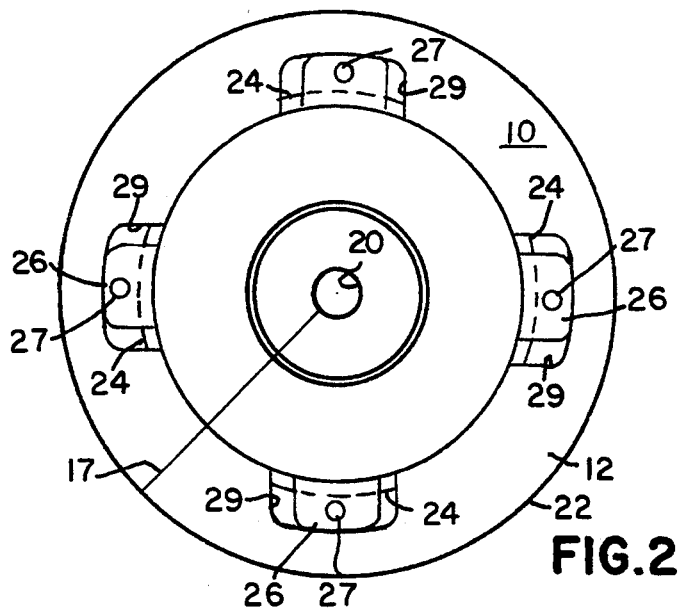
FIG. 2A is a view taken along the lines IIA—IIA of FIG. 2.
Figure 3:
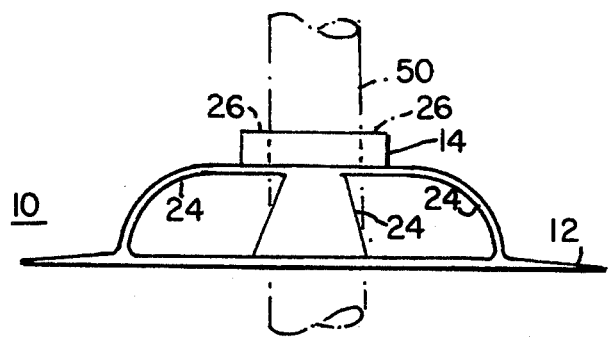
FIG. 3 is a side elevational view of the base unit of FIG. 2, in an articulated orientation.
Figure 7:
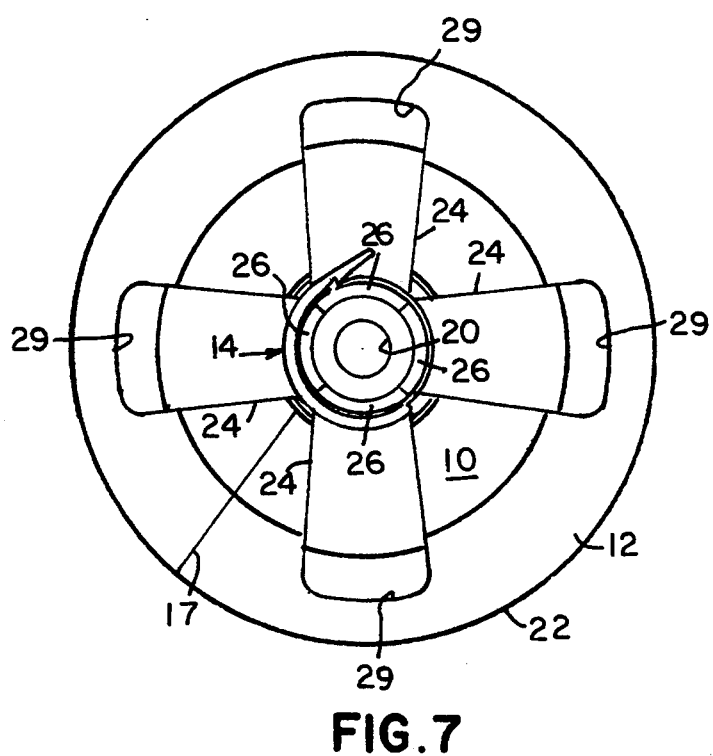
FIG. 7 is a plan view of the clamp portion arranged about the base portion of the present invention.

Referring now to the drawings, and particularly to FIG. 1, there is shown a stability device 10, comprising a base 12 and an articulable clamp 14 or brace arranged on the base 12. The base 12, also shown in a side view in FIG. 2 and in plan view in FIG. 2A, is comprised of a thin, flexible, planar member, shown here as a disc, made from an injected molded thermoplastic elastomer. The base 12 being defined by an outer edge 22 and an inner opening 20. A plurality of spaced apart flexible legs 24 extend upwardly from points mid-radius of the base 12, as shown in FIG. 2A. Openings 29 are molded through the planar base 12, as shown in FIGS. 1, 2A and 7, to facilitate injection molding of the legs 24 when the base 12 itself is injection molded. Each leg 24 has short tab 26 extending perpendicular thereto, at its distalmost tip, as shown in FIG. 2. Each tab 26 has at least one hole 27 arranged therethrough for receipt of a retaining pin(s) 46 or button(s) on clamp 14, defined hereinbelow. Each leg 24 is flexible enough so as to twist, bend or lean with respect to the base 12. The legs 24 will, in use, be bent primarily as shown in FIG. 3, with the distal tabs 26 extending perpendicular to the base 12. The base 12, is shown in FIG. 3, with the clamp 14 attached around a medical device 50, shown for exemplary purposes as a tube 50, in phantom lines in FIG. 3.

The base 12 may have a slit 17 extending from its central inner opening 20 outwardly to its outer edge 22, as shown in FIG. 2A, to permit the stability device 10 to be applied to a patient after a trocar, catheter, or other medical device is already in place.

Figure 4:
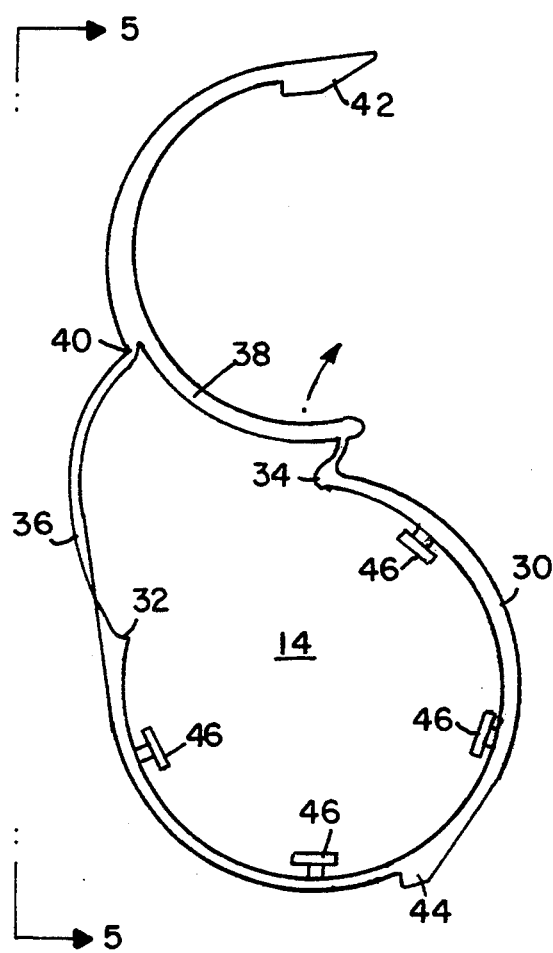
FIG. 4 is a plan view of an open clamp portion of the present invention.
Figure 5:
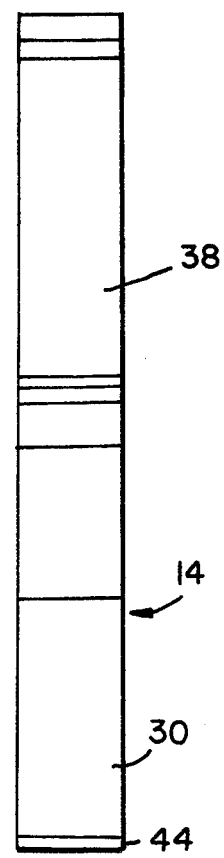
FIG. 5 is a view taken along lines V—V of FIG. 4.

The clamp 14 is a hingedly articulable plastic member, molded initially somewhat like a closed loop somewhat in the shape of a figure "6", as shown in FIG. 4. The clamp 14 has a flexible first annular portion 30 having a first and a second end, 32 and 34. The first end 32 has an arcuate band 36 flexibly thereattached. The second end 34 has a semicircular band 38 hingedly thereattached. The other end of the arcuate band 36 being hingedly attached to a mid-point 40 of the semicircular band 38 with a locking barb 42 at its distal end.

Figure 6:
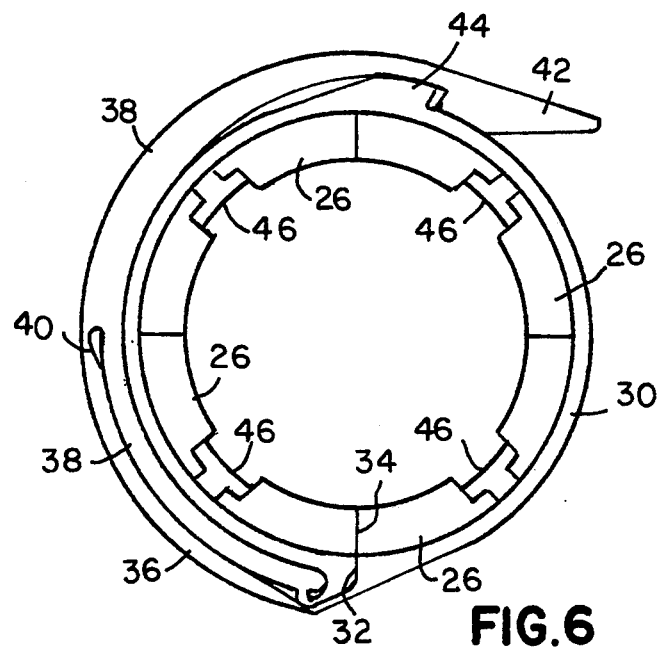
FIG. 6 is a plan view of the clamp portion of the present invention, in a closed configuration.

A corresponding engaging locking barb 44 is molded onto the outer mid-point of the first annular portion 30, as shown in FIGS. 4 and 6.

The semi-circular band 38 is pivotable about the second end 34 so as to bring the semi-circular band 38 into juxtaposition adjacent the outside periphery of the first annular portion 30, permitting its lockable barb 42 and the locking barb 44 on the first annular portion to engage one another, while simultaneously bringing the first and second ends 32 and 34 into abutting contact, as shown in FIGS. 1, 6 and 7, accomplishing a reduction in the diameter of the first annular portion 30.

The clamp 14 is thus brought into binding engagement about the tabs 26 on the end of each bent leg 24, as shown in plan view in FIG. 7, and in a side view in FIG. 3. The vertical dimension of the clamp 14 is approximately equal to the length of the tabs 26. The first annular portion 30 has the plurality of spaced apart pins 46, which when the first and second ends 32 and 34 are butted together, align with the holes 27 in the tabs 26 and permit secure engagement therewith.

Figure 8:
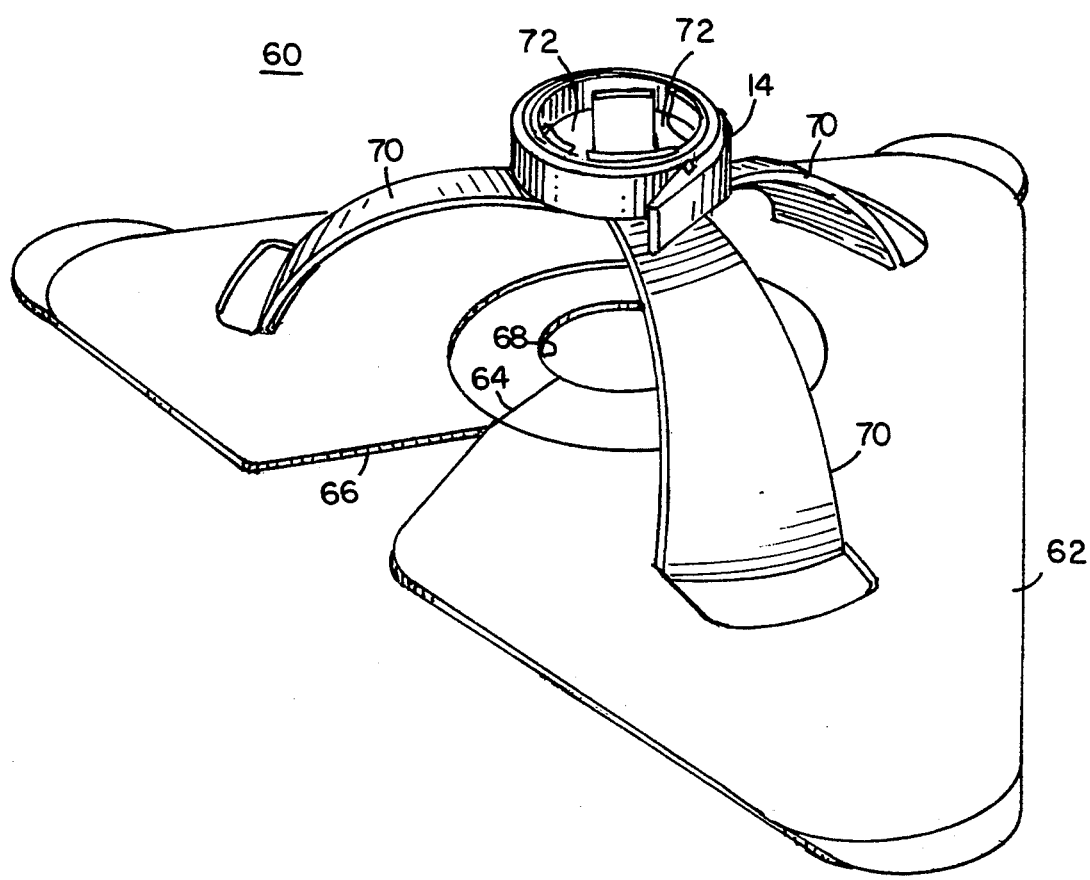
FIG. 8 is a perspective view of a stability device having an alternatively arranged base and leg setup.

FIG. 8 shows a stability device 60, having a multi-sided (here a triangularly shaped) base 62, with a notch 66, and a slit 64 which provides access to a central opening 68 in that base 62, through which stability device 60, a medical device may be maintained. In this embodiment, three legs 70 are shown which each have a tab 72 attached with a clamp 74 in a manner similar to the above-described embodiments.

The stability device 10 or 60 may be attachable itself to the body wall (skin) of a patient, preferably through a tissue engagable adhesive disposed on the bottomside (the side opposite from which the legs extend) of the base 12 or 62, or the base may be attached to the patient's skin by suture or tape, for clarity purposes not shown.

The medical device 50, as shown in exemplary manner in FIG. 3, may be clamped securely by the stability device 10, holding that tubular member 50 in engagement with a patient/body surface to which it is adhered. The stability device 10 or 60 may be arranged about a medical device either before or after that device is inserted into a patient, the slit making it more convenient to apply the device 10 or 60 around the medical device.

The legs 24 of the base 12 permit a flexibility and slight movement or twist between any captured medical device 50 and the patient to which the stability device is attached.

The clamp 14, being molded in its "open" position, as shown in FIG. 4, has a natural bias to return to that configuration if the interlocking barbs 42 and 44 are unlocked. The device 10 permits any wound or surgical opening to be clear of adhesive and able to get air, inspection by medical personal, yet maintain communication with the treatment being delivered by such member 50.

I claim:

1. A stability device for holding a medical device onto a patient, while permitting resilient flexibility and cleanliness of a surgical site, said device comprising:
  a planar, flexible base having a central inner opening and an outer peripheral edge;
  a plurality of spaced apart flexible legs each extending from a proximal location on one side of said planar, flexible base, each of said legs having a distal end; and
  a diametrically contractable clamp arrangable about the distal ends of said legs so as to enable a medical device to be securely engaged therewithin;
  said distal end of said legs having a tab extending therefrom, which tabs are disposable between said contractable clamp and a device being secured therewithin.

2. A stability device as recited in claim 1, wherein said flexible base has an adhesive disposed on one side thereof, to permit said stability device to be attached to a body surface.

3. A stability device as recited in claim 1, wherein said flexible base is comprised of a thin circularly or multisided shaped disc.

4. A stability device as recited in claim 1, wherein said clamp has an inner periphery with a plurality of buttons or pins therein, said buttons or pins arranged to engage said tabs in a secure manner.

5. A stability device as recited in claim 1, wherein said clamp has semicircular pivotable segment which has a locking member on its distal end, to engage a corresponding locking member also arranged on said clamp.

6. A stability device as recited in claim 5, wherein said clamp is made of an injection molded plastic, in the open configuration of generally a figure "6" shape.

7. A stability device as recited in claim 5, wherein said clamp is comprised of a first annular portion having a pair of ends which meet in abutting relationship when said semicircular segment is juxtaposed in locking relationship into said first annular portion.

8. A stability device for engaging a medical device entering the body of a patient to which said stability device is attached, comprising:
  a flexible planar base arranged in a spaced relationship to a medical device entering a body;
  a plurality of spaced apart flexible legs having proximal portions attached to said base and also having distal ends extending from said flexible base;
  a tab member arranged on the distal end of each of said legs and disposed perpendicular thereto, said tabs having holes therethrough for securement purposes; and
  a clamp means tightenable about said tabs on the distal ends of said flexible legs so as to securely hold said legs onto any medical device disposed therewithin, said clamp having a spaced array of buttons or pins on its inner periphery, to engage said holes in said tabs on the distal end of said legs for securement therebetween.

9. A stability device as recited in claim 8, wherein said clamp has a locking means to hold it fixedly closed about said legs and a member enclosed therewithin.

10. A stability device as recited in claim 8, wherein said planar base is of generally circular disc shape.

11. A stability device as recited in claim 8, wherein said planar base is of generally triangular shape.

12. A stability device as recited in claim 8, wherein said planar base is a multi-sided member.

13. A stability device as recited in claim 8, wherein said flexible base has a slit extending from its central opening outwardly therefrom.

14. A method of stabilizing a medical device with respect to a patient receiving a medical device through a body wall, comprising the steps of:
  providing a spread open clamp attached to a flexible, planar base member having an outer periphery, comprising a base of a stability device;
  providing said flexible, planar member with a plurality of flexible upstanding legs thereon extending between said base and said clamp, each of said legs having a distal end with a tab extending perpendicular thereto, said base having a central opening therethrough, said base having a slit extending from its central opening outwardly to its outer periphery;
  arranging said base member adjacent the medical device extending from the patient;
  spreading apart said flexible planar member on a split thereacross, so as to engage the medical device in said central opening of said planar member;
  bending said flexible legs so that said tabs on their distal ends engage the medical device;
  pivoting a closing clamp about said tabs on said distal ends of said legs so as to engage the medical device and tabs within said clamp; and
  locking said clamp about said tabs on said distal ends of said legs to engage the medical device member therewithin.

15. The method of claim 14, including the step of:
  engaging said stability device about said medical device after said medical device is already inserted in a patient.

16. The method of claim 14, including the step of:
  engaging said stability device about said medical device before said medical device is inserted in a patient.

17. The method of claim 14, including the step of:
  arranging a tissue engaging adhesive on the lowermost side of said planar base, to permit adhesive securement of said stability device to a patient utilizing said device.

18. The method of claim 14, including the step of:
  attaching said stability device to a patient through suturing or taping of said base to the patient.

19. A stability device for holding a medical device onto the body wall or skin of a patient, while permitting resilient flexibility and cleanliness of a surgical site in that body wall, said device comprising:

a molded securement arrangement for engaging the medical device with respect to the body wall of the patient; and a diametrically contractable clamp arrangable about said securement arrangement and said medical device so as to enable a medical device to be securely engaged therewithin;

said clamp being a closed loop having a semicircular pivotable segment which has a locking member on its distal end, to engage a corresponding locking member also arranged on said clamp;

said clamp being made of an injection molded plastic, in the open configuration of generally a figure "6" shape;

20. A stability device as recited in claim 19, wherein said clamp is comprised of a first annular portion having a pair of ends which meet in abutting relationship when said semicircular segment is juxtaposed in locking relationship into said first annular portion.

* * * * *